(12) United States Patent
Kim et al.

(10) Patent No.: US 12,212,918 B2
(45) Date of Patent: Jan. 28, 2025

(54) ELECTRONIC DEVICE

(71) Applicant: LG ELECTRONICS INC., Seoul (KR)

(72) Inventors: Eujin Kim, Seoul (KR); Wonseok Joo, Seoul (KR); Sungin Choi, Seoul (KR); Jungyun Lee, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 347 days.

(21) Appl. No.: 17/809,359

(22) Filed: Jun. 28, 2022

(65) Prior Publication Data

US 2023/0269523 A1 Aug. 24, 2023

(30) Foreign Application Priority Data

Feb. 22, 2022 (KR) .................. 10-2022-0022840

(51) Int. Cl.
*H04R 1/10* (2006.01)
*A45C 11/00* (2006.01)
(Continued)

(52) U.S. Cl.
CPC ............ *H04R 1/1091* (2013.01); *A45C 11/00* (2013.01); *A45C 15/06* (2013.01); *A61L 2/10* (2013.01); *A61L 2/26* (2013.01); *H04R 1/1016* (2013.01); *H04R 1/1041* (2013.01); *H05K 1/0274* (2013.01); *A45C 2011/001* (2013.01); *A61L 2202/11* (2013.01); *A61L 2202/182* (2013.01); *H04R 2420/07* (2013.01); *H05K 2201/10106* (2013.01); *H05K 2201/10121* (2013.01)

(58) Field of Classification Search
CPC .. H04R 1/1091; H04R 1/1016; H04R 1/1041; H04R 2420/07; H04R 1/1025; H04R 1/10; A45C 11/00; A45C 15/06; A45C 2011/001; A61L 2/10; A61L 2/26; A61L 2202/11; A61L 2202/182; A61L 2202/122; H05K 1/0274; H05K 2201/10106; H05K 2201/10121; H05K 1/028; F21V 33/0052; G06F 1/163
See application file for complete search history.

(56) References Cited

U.S. PATENT DOCUMENTS

| 8,597,588 B1 * | 12/2013 | Trabalka .................. A61L 2/10 |
| | | 250/455.11 |
| 2016/0083271 A1 * | 3/2016 | Chen ...................... C02F 1/325 |
| | | 250/432 R |
| 2017/0319725 A1 * | 11/2017 | Hann ....................... A61L 2/10 |

FOREIGN PATENT DOCUMENTS

| CN | 206894268 U | * | 1/2018 |
| CN | 208241838 U | * | 12/2018 |
| (Continued) | | | |

OTHER PUBLICATIONS

European Patent Office Application Serial No. 22198293.7, Search Report dated Oct. 4, 2023, 16 pages.

*Primary Examiner* — David E Smith
*Assistant Examiner* — Christopher J Gassen
(74) *Attorney, Agent, or Firm* — LEE, HONG, DEGERMAN, KANG & WAIMEY

(57) ABSTRACT

An electronic device includes a holder, a light emitting unit, and a housing. The holder includes a head holder in which a head of a wearable device is mounted, and a body holder in which a body of the wearable device is disposed. The light emitting unit emits light toward the head holder. The housing surrounds the holder and the light emitting unit.

9 Claims, 12 Drawing Sheets

(51) Int. Cl.
     *A45C 15/06*    (2006.01)
     *A61L 2/10*     (2006.01)
     *A61L 2/26*     (2006.01)
     *H05K 1/02*     (2006.01)

(56) References Cited

FOREIGN PATENT DOCUMENTS

| | | | |
|---|---|---|---|
| CN | 209862582 | | 12/2019 |
| CN | 209882008 U | * | 12/2019 |
| CN | 212163672 | | 12/2020 |
| WO | 2020227771 | | 11/2020 |

* cited by examiner (a)            (b)

(a)

(b)

(c)

(a)

(b)

(b)

(b)

ELECTRONIC DEVICE

CROSS-REFERENCE TO RELATED APPLICATIONS

Pursuant to 35 U.S.C. § 119(a), this application claims the benefit of earlier filing date and right of priority to Korean Patent Application No. 10-2022-0022840, filed on Feb. 22, 2022, the contents of which are hereby incorporated by reference herein in their entirety.

BACKGROUND OF THE INVENTION

Field of the Invention

The present disclosure relates to an electronic device, and more particularly to an electronic device in which a wearable device is charged, mounted, and/or stored.

Discussion of the Related Art

An electronic device (hereinafter referred to as an audio (or sound) output device) that outputs an audio (or sound) signal is a type of device that converts electrical energy into acoustic energy, and is connected to various multimedia devices by wire or wirelessly, thereby outputting sound.

The audio output device may be, for example, an earphone, a speaker, or the like. The earphone is an audio (or sound) output device designed to be mounted on the user's ear, and is a device for outputting sound by transmitting vibrations to the eardrum of the ear without emitting sound into the space. The speaker is a device that emits sound by emitting sound corresponding to sound energy into the space.

According to earphone operation methods, the earphones can be classified into a wired earphone for receiving an audio (or sound) signal from an external device through a wire, and a wireless earphone for receiving a sound signal from an external device through wireless communication such as Bluetooth. At this time, the wired earphone having a wire is generally wound up and stored when not in use, and also need not be charged with electricity. In contrast, the wireless earphone generally requires a separate case in which the wireless earphone can be stored when not in use.

On the other hand, as the wearing time of the earphones worn by users increases, the number of occurrences of otitis externa of the users who are wearing the earphones is rapidly increasing. The reason why the otitis externa occurs due to the earphone is as follows. When the user wears the earphone, the eartip of the earphone blocks the user's earhole so that air circulation in the user's earhole becomes difficult and the humidity inside the ear increases, thereby creating an undesirable environment in which bacteria easily produce in the user's earhole.

SUMMARY OF THE INVENTION

Accordingly, the present disclosure is directed to an electronic device that substantially obviates one or more problems due to limitations and disadvantages of the related art.

An object of the present disclosure is to provide an electronic device for sterilizing at least a portion of a wearable device mounted in the electronic device.

Another object of the present disclosure is to provide an electronic device for sterilizing the inside or outside of an eartip of a wearable device.

Another object of the present disclosure is to provide an electronic device with improved appearance quality because sterilization components are concealed.

Another object of the present disclosure is to provide an electronic device capable of implementing waterproofing.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, an electronic device may include a holder configured to include a head holder in which a head of a wearable device is mounted, and a body holder in which a body of the wearable device is disposed; a light emitting unit configured to emit light toward the head holder; and a housing configured to surround the holder and the light emitting unit. The holder includes a first holder in which the first wearable device is mounted and a second holder in which the second wearable device is mounted, and the light emitting unit is disposed between the first holder and the second holder.

The light emitting unit may include: a wiring substrate; a light source formed on the wiring substrate, and electrically connected to the wiring substrate to emit light; and a lens configured to surround the light source and formed on the wiring substrate.

The wiring substrate may include a first surface, a second surface, and a bent portion for connecting the first surface to the second surface; and the light source includes a first light source disposed on the first surface to emit light toward a first head holder, and a second light source disposed on the second surface to emit light toward a second head holder.

At least a portion of the lens may be formed as a concave surface.

The lens may be formed of a material having an ultraviolet (UV) transmittance greater than or equal to a preset transmittance.

The light emitting unit may be formed by coupling the lens to the wiring substrate in which the light source is disposed, waterproofing the lens, and connecting to the holder.

The light emitting unit may be formed to be tilted by a preset angle or less with respect to a central axis of the head holder.

The light source may emit light at a predetermined irradiation angle toward the lens.

The holder may further include a guide formed to fix the wearable device such that the light emitting unit and the head of the wearable device are spaced apart from each other by a predetermined distance or more.

At least a portion of the inside of the head holder may include a reflection unit formed to reflect light emitted from the light emitting unit.

The electronic device may further include a sensor configured to sense whether the wearable device is located within a predetermined distance from the light emitting unit.

In accordance with another embodiment of the present disclosure, an electronic device may include a holder configured to include a head holder in which a head of a wearable device is mounted and a body holder in which a body of the wearable device is disposed; a light emitting unit configured to include a light source for emitting light toward the head holder and a lens for refracting the emitted light; and a housing configured to surround the holder and the light emitting unit.

The light emitting unit may be tilted with respect to a central axis of the head holder.

It is to be understood that both the foregoing general description and the following detailed description of the present disclosure are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings.

DESCRIPTION OF SPECIFIC EMBODIMENTS

Reference will now be made in detail to embodiments of the present disclosure, examples of which are illustrated in the accompanying drawings. Wherever possible, the same reference numbers will be used throughout the drawings to refer to the same or like parts, and redundant description thereof will be omitted. As used herein, the suffixes "module" and "unit" are added or used interchangeably to facilitate preparation of this specification and are not intended to suggest distinct meanings or functions.

Further, in describing the embodiments disclosed in this specification, if a detailed description of related known techniques would unnecessarily obscure the gist of the embodiments disclosed in this specification, detailed description thereof will be omitted. In addition, the attached drawings are provided for easy understanding of the embodiments disclosed in this specification and do not limit technical idea disclosed in this specification, and the embodiments should be construed as including all modifications, equivalents, and alternatives falling within the spirit and scope of the present disclosure.

Terms including ordinal numbers such as first, second, etc. may be used to explain various elements. However, it will be appreciated that the elements are not limited to such terms. These terms are merely used to distinguish one element from another. Stating that one constituent is "connected" or "linked" to another constituent should be understood as meaning that the one constituent may be directly connected or linked to the other constituent or another constituent may be interposed between the constituents.

On the other hand, stating that one constituent is "directly connected" or "directly linked" to another should be understood as meaning that no other constituent is interposed between the constituents. As used herein, the singular forms "a", "an", and "the" include plural referents unless context clearly dictates otherwise. In this specification, terms such as "includes" or "has" are intended to indicate existence of characteristics, figures, steps, operations, constituents, components, or combinations thereof disclosed in the specification. The terms "includes" or "has" should be understood as not precluding possibility of existence or addition of one or more other characteristics, figures, steps, operations, constituents, components, or combinations thereof.

Figure 1:
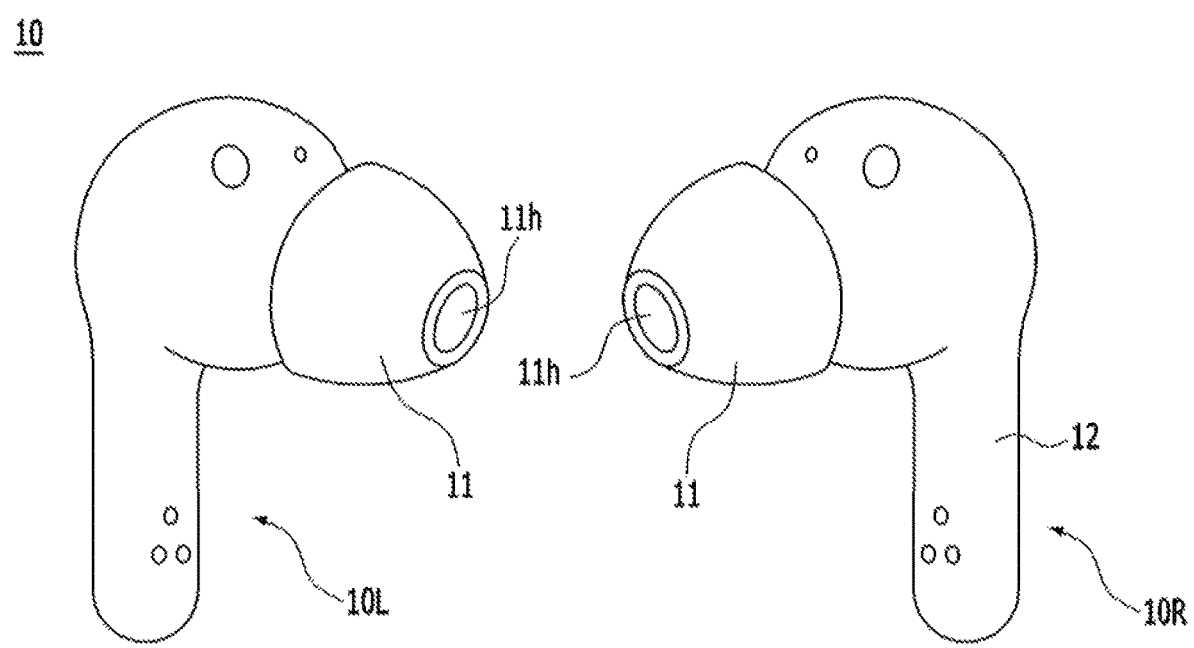
FIG. 1 is a diagram illustrating an example of a wearable device according to the embodiments of the present disclosure.

FIG. 1 is a diagram illustrating an example of a wearable device according to the embodiments of the present disclosure.

In FIG. 1, reference numeral 10 denotes a wearable device. The wearable device 10 is an electronic device that can be worn by a user, and is mounted in the electronic device (200, see FIG. 3) according to the embodiments of the present disclosure.

The wearable device 10 may be worn on the user's ear, and may include, for example, one or more earphones. For example, the wearable device 10 may convert an electrical signal including information on sound into an audio signal through vibration, and may output the audio signal. The wearable device 10 may include both a device for outputting an input electrical signal only as an audio (sound) signal and a device for outputting the input electrical signal as sound, images, or other data based on other methods. Although FIG. 1 illustrates a canal-type earphone as an example of the wearable device 10, the wearable device 10 includes open-type earphone(s).

Although not shown, the wearable device 10 may include a communication unit and an audio output unit. The wearable device 10 may receive a signal including sound information and the like from an external device through the communication unit. At this time, the communication unit is a module capable of transmitting and receiving data through wireless communication. In addition, the wearable device 10 may output the received signal as an audio signal through the audio output unit.

In this case, the external device that transmits/receives data to and from the wearable device 10 may be, for example, a multimedia device. The multimedia device may include, for example, a mobile phone, a smartphone, a laptop, a digital broadcasting terminal, a personal digital assistant (PDA), a portable multimedia player (PMP), a navigation system, a slate PC, a tablet, an ultrabook, a digital TV, a desktop computer, and the like.

The wearable device 10 may further include a power-supply unit. The power-supply unit may charge, store, and discharge power by a predetermined capacity. At this time, the wearable device 10 may perform charging by receiving power from the electronic device 200 through the power-supply unit according to the embodiments.

Although FIG. 1 illustrates a wireless wearable device that transmits and receives data through a wireless communication unit for convenience of description, the wearable device 10 may also be implemented as a wired wearable device that transmits and receives data through a wired communication unit. In this case, the purpose of accommodating the wearable device in the electronic device according to the embodiments described below is focused on sterilization rather than storage convenience while the electronic device including the wearable device is carried by the user.

When the wearable device 10 is worn on both ears of the user, the wearable device 10 may include, for example, a first wearable device 10L worn on the left ear and a second wearable device 10R worn on the right ear. The first wearable device 10L and the second wearable device 10R are respectively inserted into the left earhole and the right earhole of the user, so that the wearable device 10 including the first wearable device 10L and the second wearable device 10R can be worn by the user.

Specifically, the wearable device 10 may include a head 11 and a body 12 connected to the head 11. The head 11 may be inserted into the earhole in the direction from the user's pinna to the user's external auditory meatus. Thus, the head 11 may be in contact with the outside and/or inside of the user's earhole. The body 12 is not inserted into the earhole, and supports the wearable device 10 to be fixed from the outside of the earhole. For example, as shown in FIG. 1, the body 12 of the wearable device 10 may be formed in a shape in which a rod extends in one direction from the head 11 and is fixed to the ear. Alternatively, unlike FIG. 1, the body 12 may be connected to the head 11, so that the body 12 may be formed in a shape that is hung or fixed to the user's earhole, so that the body 12 can be worn on the user's ear.

In this case, the head 11 may include a headhole 11h for outputting sound. The headhole 11h may be formed in a hole or passage shape in order to prevent the sound from being dispersed while the output audio signal is transferred toward the earhole. That is, the headhole 11h may be formed in a shape that is more concavely recessed toward the inside of the head 11 compared to the outside of the head 11. Due to this headhole shape, the outside of the head 11 may seal the external auditory meatus, and the headhole 11h may transmit an audio signal to the eardrum through the external auditory meatus.

However, as the inside of the head 11 is completely or partially completely sealed, the environment in which bacteria easily multiply in the external auditory meatus may occur due to the increasing humidity in the user's earhole. In addition, bacteria may also reproduce in the wearable device 10.

Accordingly, a method of sterilizing the wearable device 10 is required. Hereinafter, an electronic device capable of sterilizing the wearable device 10 will be described.

Figure 2:
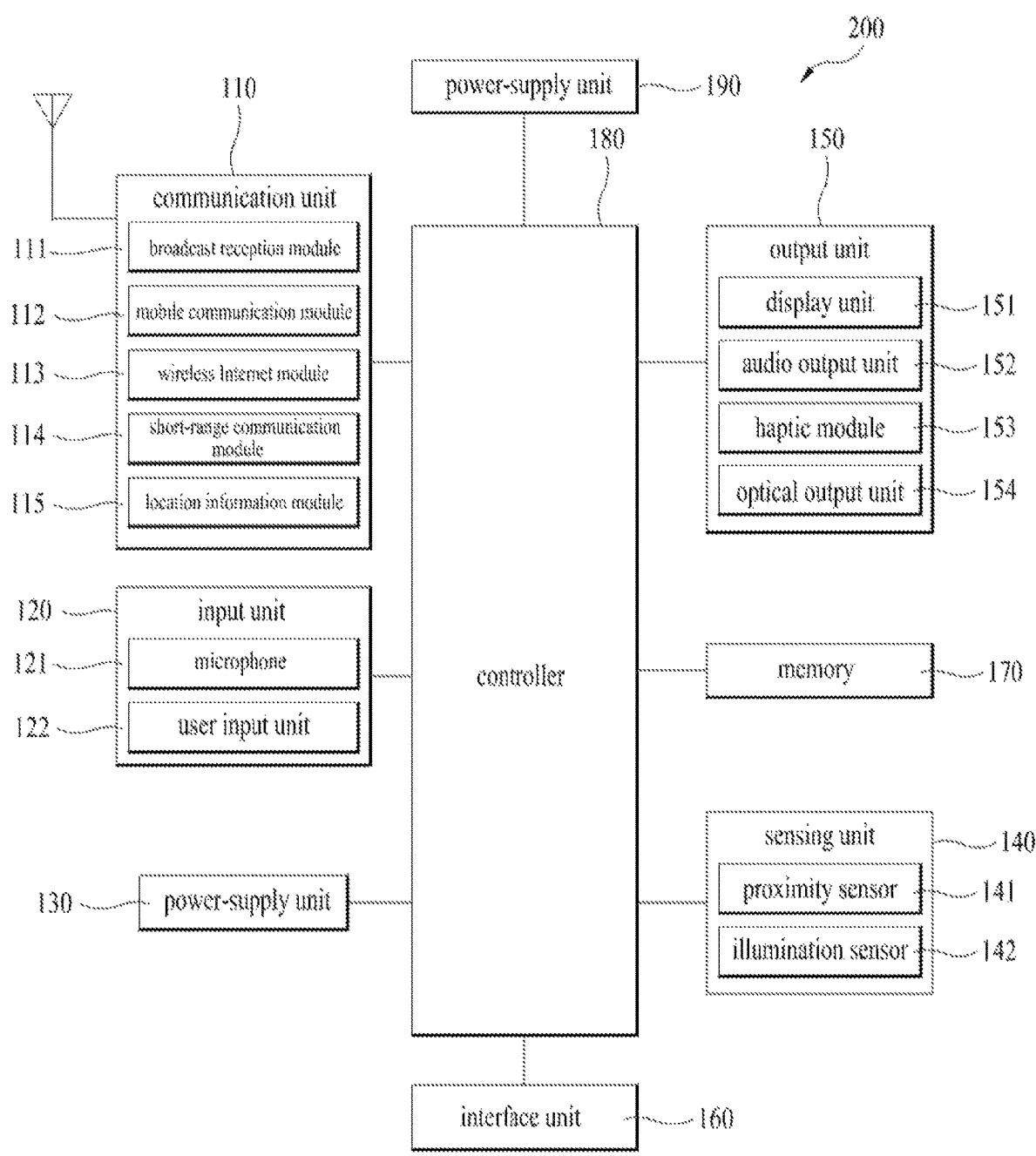
FIG. 2 is a block diagram illustrating an electronic device according to embodiments of the present disclosure.

FIG. 2 is a block diagram illustrating an electronic device 200 according to embodiments of the present disclosure.

Referring to FIG. 2, the electronic device 200 may include a communication unit 110, an input unit 120, a power-supply unit 130, a sensing unit 140, an output unit 150, an interface unit 160, a memory 170, a controller 180, a power-supply unit 190, etc. The constituent elements shown in FIG. 2 are not always required to implement the audio output device, such that it should be noted that the audio output device according to the embodiments of the present disclosure may include more or fewer components than the elements listed above.

The communication unit 110 according to embodiments may include at least one module for implementing wired or wireless communication between the electronic device 200 and the wearable device 10, wired or wireless communication between the electronic device 200 and the wired/wireless communication system, and wired or wireless communication between the electronic device 200 and the multimedia device. In addition, the communication unit 110 may include at least one module for connecting the electronic device 200 to at least one network.

However, it will be readily apparent to those skilled in the art that the communication unit 110 can communicate with the electronic device 200 according to embodiments in so far as the electronic device 200 implemented as a new product to be developed later can perform wireless communication with another device.

The communication unit 110 may include at least one of a broadcast reception module 111, a mobile communication module 112, a wireless Internet module 113, a short-range communication module 114, and a location information module 115.

The broadcast reception module 111 receives a broadcast signal and/or broadcast-related information from an external broadcast management server on a broadcast channel. The broadcast channel includes a satellite channel and a terrestrial channel. Two or more of the broadcast reception modules may be provided in the electronic device 200 for simultaneous broadcast reception or broadcast channel switching for at least two broadcast channels.

The mobile communication module 112 may transmit and/or receive wireless signals to and from one or more network entities. Typical examples of a network entity include a base station, an external mobile terminal, a server, and the like. Such network entities form part of a mobile communication network, which is constructed according to technical standards or communication methods for mobile communications (for example, Global System for Mobile Communication (GSM), Code Division Multi Access (CDMA), CDMA2000 (Code Division Multi Access 2000), EV-DO (Enhanced Voice-Data Optimized or Enhanced Voice-Data Only), Wideband CDMA (WCDMA), High Speed Downlink Packet access (HSDPA), HSUPA (High Speed Uplink Packet Access), Long Term Evolution (LTE), LTE-A (Long Term Evolution-Advanced), and the like).

The wireless signal includes various types of data according to transmission/reception of a voice signal, a video call signal, or a text/multimedia message.

The wireless Internet module 113 according to embodiments may refer to a module for wireless Internet connection, and may be installed inside or outside the electronic device 200. The wireless Internet module 113 may be configured to transmit and receive radio frequency (RF) signals over a communication network according to wireless Internet technologies.

Examples of such wireless Internet access include Wireless LAN (WLAN), Wireless Fidelity (Wi-Fi), Wi-Fi Direct, Digital Living Network Alliance (DLNA), Wireless Broadband (WiBro), Worldwide Interoperability for Microwave Access (WiMAX), High Speed Downlink Packet Access (HSDPA), HSUPA(High Speed Uplink Packet Access), Long Term Evolution (LTE), LTE-A (Long Term Evolution-Advanced), and the like.

The wireless Internet module 113 may transmit/receive data according to one or more of such wireless Internet technologies, and other Internet technologies as well.

In some embodiments, when the wireless Internet access is implemented according to, for example, WiBro, HSDPA, HSUPA, GSM, CDMA, WCDMA, LTE, LTE-A and the like, as part of a mobile communication network, the wireless Internet module 113 performs such wireless Internet access. As such, the Internet module 113 may cooperate with, or function as, the mobile communication module 112.

The short-range communication module 114 is configured to facilitate short-range communications. Suitable technologies for implementing such short-range communications include Bluetooth™, Radio Frequency IDentification (RFID), Infrared Data Association (IrDA), Ultra-WideBand (UWB), ZigBee, Near Field Communication (NFC), Wireless-Fidelity (Wi-Fi), Wi-Fi Direct, Wireless Universal Serial Bus (USB), and the like.

The short-range communication module 114 may support wireless communication between the electronic device 200 and the wearable device 10 over a wireless wide area network (WWAN), may support wireless communication between the electronic device 200 and the other electronic device over the WWAN, and may support wireless between the electronic device 200 and a network in which the other audio output device (or an external server) is disposed. The WWAN may be a wireless personal area network (WPAN).

The location information module 115 according to embodiments is a module for acquiring the location (or current location) of the electronic device 200. A representative example of the location information module 115 may be a GPS module or a Wi-Fi module.

For example, when the electronic device 200 utilizes the GPS module, the electronic device 200 may acquire the location of the electronic device 200 using a signal transmitted from a GPS satellite. As another example, when the audio output device utilizes the Wi-Fi module, the location of the audio output device can be obtained based on information of a wireless access point (WAP) that transmits or receives RF signals to and from the Wi-Fi module. If necessary, the location information module 115 may perform any function among the other modules of the communication unit 110 so as to perform a substitution operation or additionally obtain data related to the location of the audio output device.

The location information module 115 may be a module used to obtain the location (or current location) of the electronic device 200, and is not limited to a module that directly calculates or obtains the location of the electronic device 200.

The user may recognize the location of the electronic device 200 through the location information module 115. For example, the multimedia device (e.g., the user's smartphone) of the user may receive information on the location of the electronic device 200 obtained by the location information module 115 through the wireless communication unit 110. As a result, even when the electronic device 200 is lost, the user can easily find the electronic device 200.

The input unit 120 includes an image input unit (not shown), a microphone 121 or audio input unit (not shown) for inputting an audio signal, and a user input unit 122 (e.g., a touch key, a mechanical key, etc.) for receiving information from a user. The voice data or image data collected through the input unit 120 is analyzed and processed as a user control command.

The microphone 121 according to the embodiments may process an external audio signal into electrical voice data. The processed voice data may be utilized in various ways according to functions (or application program being executed) being performed in the electronic device 200.

Various noise cancellation algorithms for cancelling (or removing) noise generated in the process of receiving an external audio signal can be implemented in the microphone 121.

The user input unit 122 according to the embodiments serves to receive information from the user. When information is input through the user input unit 122, the controller 180 can operate the electronic device 200 to correspond to the input information.

The user input unit 122 may include a mechanical input means and a touch input means. Although not shown in the drawings, the touch input means may include, for example, a virtual key, a soft key, or a visual key which is displayed on the outside of the electronic device 200 through software processing. In addition, as one example, the user input unit 122 may include a touch sensor for performing sensing through a touch input sensor provided at the outer surface of the electronic device 200. Meanwhile, the virtual key or the visual key can be displayed on the outside of the electronic device 200 while being formed in various shapes. For example, the virtual key or the visual key may be composed of, for example, graphics, text, icon, or a combination thereof.

The power-supply unit 130 according to the embodiments may supply power to an external device. For example, the power-supply unit 130 may supply power to the wearable device 10 so that the wearable device 10 can be charged with electricity.

The sensing unit 140 according to the embodiments may include one or more sensors for sensing at least one of information about the inside of the electronic device 200 and the surrounding environment information on the surroundings of the electronic device 200.

In addition, the sensing unit 140 may sense information about the wearable device 10. Here, the information about the wearable device 10 may include information indicating whether the wearable device 10 is approaching or not, and information indicating whether the wearable device 10 is located at a predetermined position.

For example, the sensing unit 140 may alternatively or additionally include other types of sensors or devices, such as a proximity sensor 141 and an illumination sensor 142, a touch sensor, an acceleration sensor, a magnetic sensor, a G-sensor, a gyroscope sensor, a motion sensor, an RGB sensor, an infrared (IR) sensor, a finger scan sensor, a ultrasonic sensor, a microphone 122, a battery gauge, an environment sensor (for example, a barometer, a hygrometer, a thermometer, a radiation detection sensor, a thermal sensor, and a gas sensor, among others), and a chemical sensor (for example, an electronic nose, a health care sensor, a biometric sensor, and the like), to name a few.

On the other hand, the electronic device 200 may be utilized by combining information sensed by at least two of the above-described sensors.

The output unit 150 according to the embodiments may generate output signals related to visual, auditory, tactile sensation, or the like. The output unit 150 may include at least one of a display unit 151, an audio output unit 152, a haptic module 153, and an optical output unit 154. For example, the output unit 150 may be implemented at the exterior of the electronic device 200.

The display unit 151 may construct a mutual layer structure along with a touch sensor, or may be formed integrally with the touch sensor, such that the display unit 151 can be implemented at the exterior of the electronic device 200. The exterior of the electronic device 200 may serve as a user input unit 122 that provides an input interface between the electronic device 200 and the user, and at the same time may provide an output interface between the electronic device 200 and the user. For example, the display unit 151 may be formed outside (e.g., a housing to be described later) the electronic device 200. For example, the display unit 151 may display icons, text, etc.

The audio output module 152 is generally configured to output audio data. Such audio data may be obtained from any of a number of different sources, such that the audio data may be received from the wireless communication unit 110 or may have been stored in the memory 170. The audio data may be output during modes such as a call signal reception mode, a call mode, a record mode, a voice recognition mode, a broadcast reception mode, and the like. The audio output module 152 can provide audible output related to a particular function (e.g., a call signal reception sound, a message reception sound, etc.) performed by the electronic device 200. The audio output module 152 may also be implemented as a receiver, a speaker, a buzzer, or the like.

The haptic module 153 may be configured to generate various tactile effects that a user feels, perceive, or otherwise experience. A typical example of a tactile effect generated by the haptic module 153 is vibration. The strength, pattern and the like of the vibration generated by the haptic module 153 may be controlled by user selection or setting by the controller. For example, the haptic module 153 may output different vibrations in a combining manner or a sequential manner.

The optical output unit 154 can output a signal for indicating event generation using light of a light source of the electronic device 200. Examples of events generated in the electronic device 200 may include a notification sound indicating a charging state or a charging completion state, a notification sound indicating a charging state or a charging completion state, and the like.

The interface unit 160 according to the embodiments may serve as a passage for various types of external devices connected to the electronic device 200. The interface unit 160 may include at least one of an external charger port, a wired/wireless data port, a port for connecting a device equipped with an identification module, and an audio input/output (I/O) port.

As the external device is connected to the interface unit 160 of the electronic device 200, the electronic device 200 can perform appropriate control related to the connected external device.

The memory 170 may store data needed to support various functions of the electronic device 200.

The memory 170 may store a plurality of application programs (or applications) executed in the electronic device 200, and data or instructions required to operate the electronic device 200. At least some of the application programs may be downloaded from an external server through wireless communication. At least some of those application programs may be installed within the electronic device 200 at the time of being shipped for basic functions of the electronic device 200 (for example, a function of charging the wearable device 10, a function for sterilizing the wearable device 10, and other functions required for such charging and sterilization).

Meanwhile, the application programs may be stored in the memory 170, may be installed in the electronic device 200, and may be driven by the controller 180 to perform an operation (or a function) of the electronic device 200.

The memory 170 includes at least one of a volatile storage medium and a non-volatile storage medium. The memory 170 is at least one of a read only memory (ROM) and a random access memory (RAM).

In addition to the operation related to the application programs, the controller 180 may control overall operation of the electronic device 200. The controller 180 may process signals, data, and information that are input or output through the above-described constituent components, or may drive the application programs stored in the memory 170, so that the controller 180 can provide the user with appropriate information or functions or can process the appropriate information or functions.

In order to drive the application programs stored in the memory 170, the controller 180 can control at least some of the components shown in FIG. 1. Moreover, in order to drive the application programs, the controller 180 can combine at least two of the components included in the electronic device 200, and can operate the combination of the components.

For example, the controller 180 may be embedded in the electronic device 200 as a general processor such as a CPU. However, the controller 180 may control the electronic device 200 through the communication unit 110 without being physically located in the electronic device 200.

The power-supply unit 190 according to the embodiments may receive external power or internal power under control of the controller 180, such that the power-supply unit 190 may supply the received power to the constituent components included in the electronic device 200. The power-supply unit 190 may include, for example, a battery. The battery may be implemented as an embedded battery or a replaceable battery.

At least some of the components may operate in cooperation with each other to implement an operation, control, or control method of the electronic device 200 according to various embodiments described below. In addition, the operation, control, or control method of the audio output device may be implemented in the electronic device by driving at least one application program stored in the memory 170.

Figure 3:
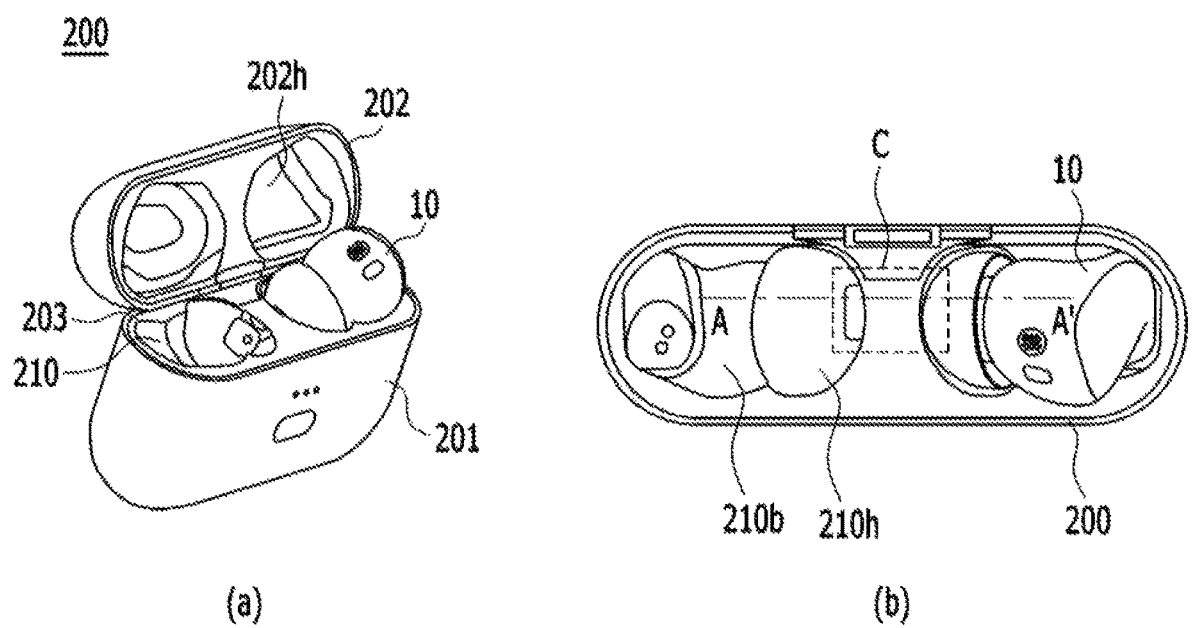
FIG. 3 is a diagram illustrating a wearable device mounted in the electronic device according to the embodiments of the present disclosure.

FIG. 3 is a diagram illustrating a wearable device mounted in the electronic device according to the embodiments of the present disclosure.

Referring to FIG. 3, the wearable device 10 may be disposed in the electronic device 200 according to the embodiments.

FIG. 3(a) is a perspective view illustrating the electronic device 200 in which the wearable device 10 is disposed.

As shown in FIG. 3(a), the electronic device 200 may include a main body 201 and a lid 202.

The main body 201 may include a holder (or a cradle) 210. The holder 210 may refer to a groove in which the wearable device 10 can be disposed in a downward direction from the main body 201. The holder 210 may be formed to correspond to the shape of the wearable device 10. That is, as shown in FIG. 3(a), the wearable device 10 may be inserted into the holder 210 and mounted in the electronic device 200.

The lid 202 may be connected to the main body 201 so as to be opened and closed. As shown in FIG. 3(a), the lid 202 has one side connected to the body 201 through a hinge part 203. The lid 202 may rotate around the main body 201 using one side connected to the main body 201 as a central axis. As a result, the lid 202 can be opened or closed with respect to the main body 201.

In a situation where the lid 202 is opened, the wearable device 10 may be disposed in the main body 201, or the wearable device 10 disposed in the main body 201 can be taken out of the main body 201.

In a situation where the lid 202 is closed, the lid 202 may prevent the wearable device 10 disposed in the main body 201 from being detached from the main body 201. In this case, the lid 202 may be fixed to the main body 201 such that the lid 202 can remain in the closed state. For example, the lid 202 may include a locking portion at the other side thereof, and the main body 201 may include a protrusion portion at the other side thereof. In this case, as the lid 202 is closed, the protrusion portion is caught by the locking portion. That is, the lid 202 is caught by the main body 201, and the inside of the electronic device 200 is closed. Alternatively, for example, each of the lid 202 and the body 201 may include a magnet on the other side thereof. As the lid 202 is closed, both magnets magnetically attract each other. That is, the lid 202 is fixed to the main body 201 by magnetic force, and the inside of the electronic device 200 is closed. Through such closing action, the electronic device 200 may prevent the wearable device 10 from being unintentionally released from the electronic device 200 even if external impact occurs.

The lid 202 may include a groove 202h. The groove 202h may be provided at a position corresponding to the holder 210. When the lid 202h is closed, the groove 202h may cover the top of the wearable device 10. At this time, the upper portion of the wearable device 10 is a portion of the wearable device 10 that is not disposed in the holder 210.

FIG. 3(b) is a top view illustrating a top portion of a main body of the electronic device 200 provided with the wearable device 10. At this time, the top portion of the main body of the electronic device 200 may refer to a top surface of the main body 201 that appears when the lid 202 is opened.

The holder 210 may include a head holder 210h in which the head 11 (see FIG. 1) of the wearable device 10 is mounted, and a body holder 210b in which the body 12 (see FIG. 1) of the wearable device 10 is mounted. The head holder 210h and the body holder 210b are physically connected to each other, and the head holder 210h and the body holder 210b may be formed in a manner that the heights of their grooves formed from the upper surface of the holder 210 may be set to the same or different values.

The wearable device 10 may be disposed in the electronic device 200 in a direction in which the heads 11 of the first and second wearable devices face each other. The wearable device 10 can be mounted and stored by the electronic device 200, and can also be charged by receiving power from the electronic device 200 as shown in FIG. 2. In addition, the wearable device 10 may be sterilized by the electronic device 200.

In this case, the electronic device 200 may sterilize the headhole 11h (see FIG. 1) of the wearable device 10. For example, the electronic device 200 may sterilize the headhole 11h of the wearable device 10 by emitting ultraviolet (UV) rays toward the headhole 11h of the wearable device 10. However, in this case, there is a problem that the outside of the head 11 contacting the user's external auditory meatus is not sterilized. On the other hand, when the number of units for emitting ultraviolet (UV) rays increases, there is a problem in that the electronic device 200 becomes too large or heavy or production costs unavoidably increase.

Accordingly, a method of maintaining or reducing the size of the electronic device 200 while sterilizing both the inside and outside of the head 11 of the wearable device 10 will hereinafter be described in detail.

Figure 4:
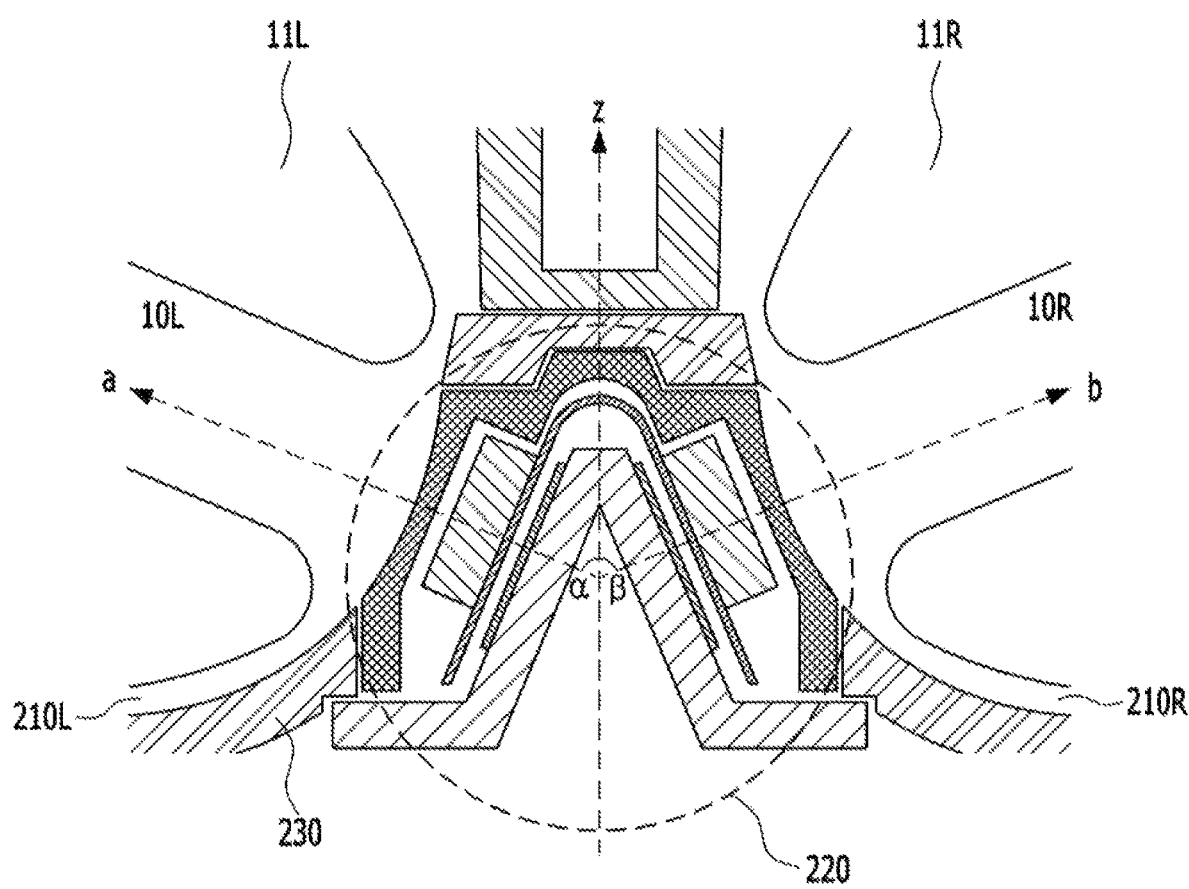
FIG. 4 is a cross-sectional view illustrating one example of the wearable device taken along the line A-A' shown in FIG. 3.

FIG. 4 is a cross-sectional view illustrating one example of the wearable device taken along the line A-A' shown in FIG. 3. In more detail, FIG. 4 is a cross-sectional view illustrating the portion "C" taken along the line A-A' of FIG. 3.

The wearable device 10 may include a pair of first wearable devices 10L and a second wearable device 10R. For example, the first wearable device 10L is a device that is worn on the user's left ear, and the second wearable device 10R is a device that is worn on the user's right ear. Unlike FIG. 4, the subject to which the embodiments are applied may be implemented not only as one pair of the first and second wearable devices, but also as only one wearable device without departing from the scope or spirit of the present disclosure.

In FIG. 4, "11L" may denote the head 11 of the left wearable device shown in FIGS. 3, and "11R" may denote the head of the right wearable device shown in FIG. 3. In more detail, "11L" may denote the head of the first wearable device 10L, and "11R" may denote the head of the second wearable device 10R. In FIG. 4, "z" denotes a central axis with respect to the height direction of the electronic device 200. In addition, "a" may denote the central axis of the head 11L of the first wearable device mounted in the electronic device 200, and "b" may denote the central axis of the head 11R of the second wearable device mounted in the electronic device 200.

The electronic device 200 may include a holder 210, a light emitting unit 220, and a housing 230.

As illustrated in FIG. 3, the holder 210 is a space in which the wearable device 10 is mounted, and the holder 310 may include a head holder 210h and a body holder 210b. In addition, the holder 210 may include a first holder 210L in which the first wearable device 10L is mounted, and a second holder 210R in which the second wearable device 10R is mounted.

The first holder 210L and the second holder 210R may be disposed opposite to each other. For example, the head holder of the first holder 210L and the head holder of the second holder 210R may be disposed close to each other. Accordingly, when the first wearable device 10L and the second wearable device 10R are received in the electronic device 200, the head 11L of the first wearable device and the head 11R of the second wearable device may be disposed close to each other.

In this case, each of the head holder of the first holder 210L and the head holder of the second holder 210R may be inclined at a predetermined angle with respect to the central axis (z) of the height direction of the electronic device 200. In this case, the first holder 210L may be inclined at a preset angle (α) with respect to the central axis (z) of the height direction of the electronic device 200, and the second holder 210R may be inclined at a preset angle (β) with respect to the central axis (z) of the height direction of the electronic device 200. Here, α is a real number between 0° and 90°, and β is a real number between 0° and 90°. In this case, the preset angle is an angle between the central axis (z) for the height direction of the electronic device 200 and the central axis of the head 11 of the wearable device disposed in the electronic device 200.

α and β may have the same value. That is, the first holder 210L and the second holder 210R may be arranged line-symmetrically to the central axis (z) of the height direction of the electronic device 200. In this case, according to the embodiments, the light emitting unit 220 may be disposed in the electronic device 200 without reducing the capacity of the power-supply unit of the electronic device 200, thereby improving space utilization and productivity.

Alternatively, α and β may have different values. In this case, each of α and β may be a real number between 0° and 90°. In this case, the embodiments of the present disclosure may consider the degree of freedom in spatial arrangement of the first holder 210L and the second holder 210R.

The light emitting unit 220 may emit light toward the head holder 210h. A method for emitting light by the light emitting unit 220 will be described later with reference to FIG. 5. The light emitting unit 220 may be disposed between the first holder 210L and the second holder 210R. The center of the light emitting unit 220 is substantially similar to the central axis of the height direction of the electronic device 200.

The housing 230 may be formed in each of the body 201 and the lid 202 illustrated in FIG. 3. The housing formed in the lid 202 may be connected to be open or closed with respect to the other housing formed in the body 201. For example, the two housings may be connected to each other through a hinge portion 203 shown in FIG. 3.

The housing 230 may form the holder 210 and support the light emitting unit 220. Specifically, the housing 230 may include a groove formed in the height direction of the electronic device 200 so that the body holder 210b can be formed in the groove. In addition, the housing 230 may further include the other groove formed in the depth direction (forward and backward direction) and the width direction (left and right direction) of the electronic device 200 so that the head holder 210h can be formed in the other groove. In addition, the housing 230 may form a space in which the light emitting unit 220 is formed under the light emitting unit 220 so that the light emitting unit 230 can be supported by the housing 230. The housing 230 may be disposed to surround the holder 210 and the light emitting unit 220 that are to be formed or supported. As a result, the housing 230 can protect, for example, all or some of the constituent elements of the electronic device 200 shown in FIG. 2 from external impact, and can provide the space in which each component can be supported or fixed.

Hereinafter, the structure of the light emitting unit 220 included in the electronic device 200 according to embodiments will be described in detail.

Figure 5:
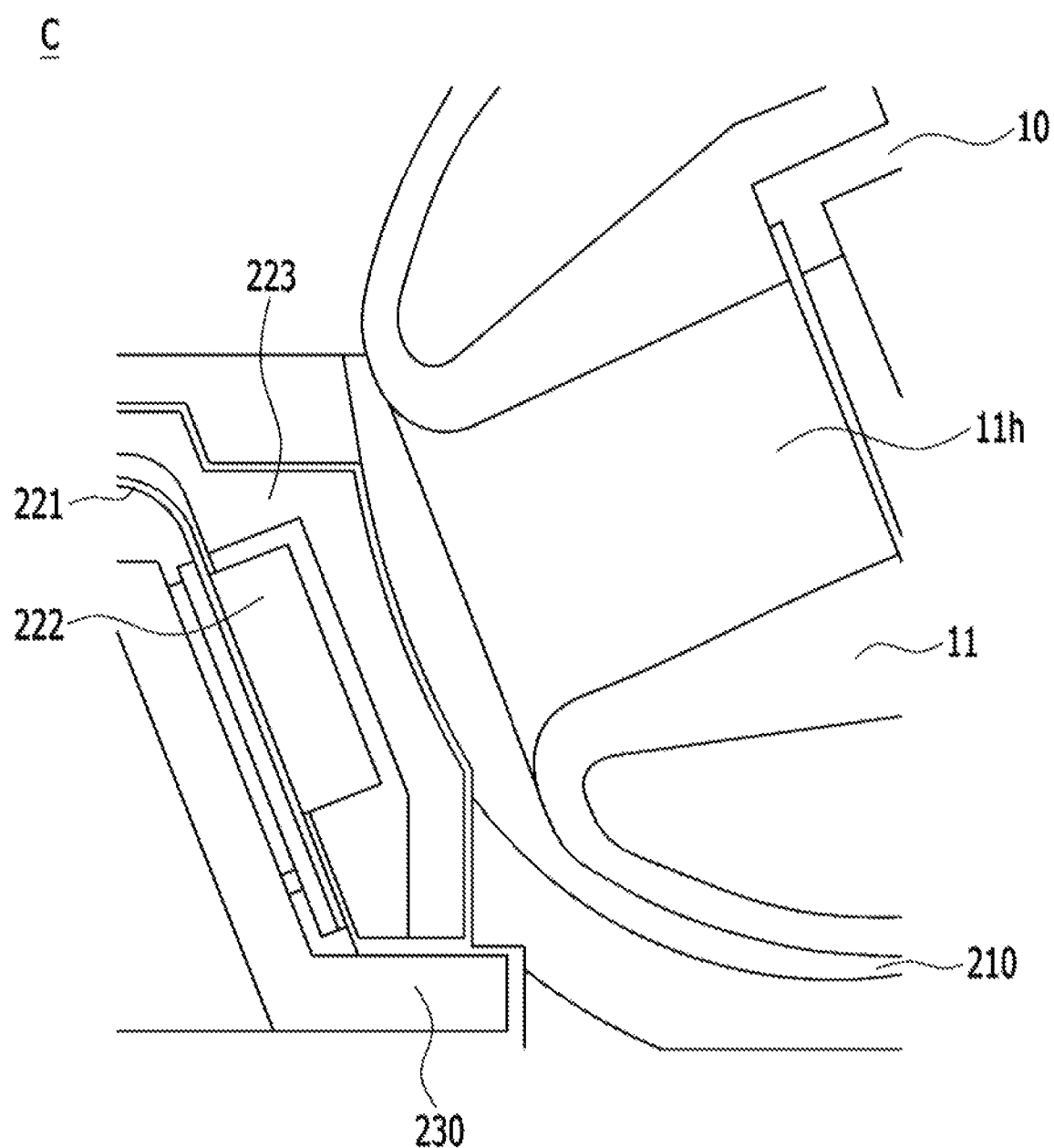
FIG. 5 is a detailed diagram illustrating the portion "C" of FIG. 3.

FIG. 5 is a detailed diagram illustrating the portion "C" of FIG. 3.

Referring to FIG. 5, the light emitting unit 220 may include a wiring substrate 221, a light source 222 formed on the wiring substrate, and a lens 223 formed to surround the light source.

The wiring substrate 221 may be disposed between the first holder 210L and the second holder 210R. The wiring substrate 221 may be formed between the first holder 210L and the second holder 210R, and may be disposed on the housing 230 surrounding a portion of the lower side of the head holder 210h.

The wiring substrate 221 is a printed circuit board (PCB) on which an electrical circuit (including an electrode, a wiring, etc.) is printed. The wiring substrate 221 may apply an electrical signal toward the light source 222.

The wiring substrate 221 may include, for example, a flexible substrate. The wiring substrate 221 may include a flexible material having insulation properties. For example, the wiring substrate 221 may include glass, polyimide (PI), polyethylene naphthalate (PEN), polyethylene terephthalate (PET), etc.

The light source 222 may be formed on the wiring substrate 221, and may be electrically connected to the wiring substrate 221. The light source 222 may convert the current received from the wiring substrate 221 into light, and may emit the converted light toward the head holder 210b. Specifically, the light source 222 may emit light toward the head 11 of the wearable device.

The light source 222 is a type of semiconductor light-emitting device (LED) that converts the current into light. For example, the light source 222 is an ultraviolet light-emitting diode (UV LED) that emits ultraviolet (UV) light. In this case, the light source 222 may conceptually include a UV LED, a UV micro-LED, and the like, and may be used interchangeably with the UV LED, the UV micro-LED, etc.

That is, light emitted from the light source 222 is, for example, ultraviolet (UV) light, and may be electromagnetic waves having a wavelength of 10 nm to 397 nm. Specifically, the light emitted from the light source 222 may include UV-C radiation having a wavelength of 100 nm to 280 nm. The light source 222 emits such light to sterilize or disinfect microorganisms present in all or some of the head 11 and/or the body 12 of the wearable device.

The light source 222 may include one UV LED, as shown in FIG. 5. That is, one UV LED may serve as the light source 222.

However, unlike FIG. 5, the light source 222 may include a plurality of UV LEDs. In this case, the plurality of UV LEDs may serve as one light source 222. When the light source 222 includes the plurality of UV LEDs, the plurality of UV LEDs may be located in one flat wiring substrate 221 that is equal to or similar to those of FIG. 5. The above-described embodiment can reduce production costs. Alternatively, the plurality of UV LEDs may be disposed in one flexible wiring substrate 221. For example, the plurality of UV LEDs may be disposed in the wiring substrate 221 convexly formed toward the head holder 11h. The above-described embodiment can allow light emitted from the light source 222 to better spread toward all portions of the head 11 of the wearable device.

The lens 223 may surround at least a portion of the light source 222, and may be formed on the wiring substrate 221.

The lens 223 may transmit light emitted from the light source 222 in the direction of the head holder 210h, and the lens 223 may refract the direction of the transmitted light. The lens 223 may refract all or some of the light emitted toward the headhole 11h so that the light can be directed toward the head 11 and/or the headhole 11h of the wearable device. In this case, the refraction may include both convergence of light and diffusion and spreading of light. That is, the lens 223 may allow the light emitted from the light source 222 to be directed toward the entire inside and outside of the head 11 of the wearable device.

The lens 223 may include a material having a high transmittance of light emitted from the light source 222. For example, the lens 223 may include a material having an ultraviolet (UV) transmittance that is equal to or greater than a predetermined transmittance. For example, the lens 223 may be formed of plastic including polymethyl methacrylate (PMMA), rubber, silicon, and the like.

Through the above-described structure, the electronic device 200 may emit light from the light emitting unit 220 such that the head 11 and/or the body 12 of the wearable device can be evenly sterilized. Accordingly, the electronic device 200 can prevent the user of the wearable device 10 mounted in the electronic device 200 from being infected with the bacteria present in the wearable device 10.

Meanwhile, although FIGS. 4 and 5 have described the case in which the light emitting unit 220 is disposed between the first holder 210L and the second holder 220R for convenience of description, the scope or spirit of the present disclosure is not limited thereto, and the light emitting unit 220 configured to use lens refraction (to be described later) can also be used in the other case in which the head holder of the first holder 210L and the head holder of the second holder 210R are not disposed close to each other.

Hereinafter, the structure and arrangement of the light emitting unit 220 will be described in detail.

Figure 6:
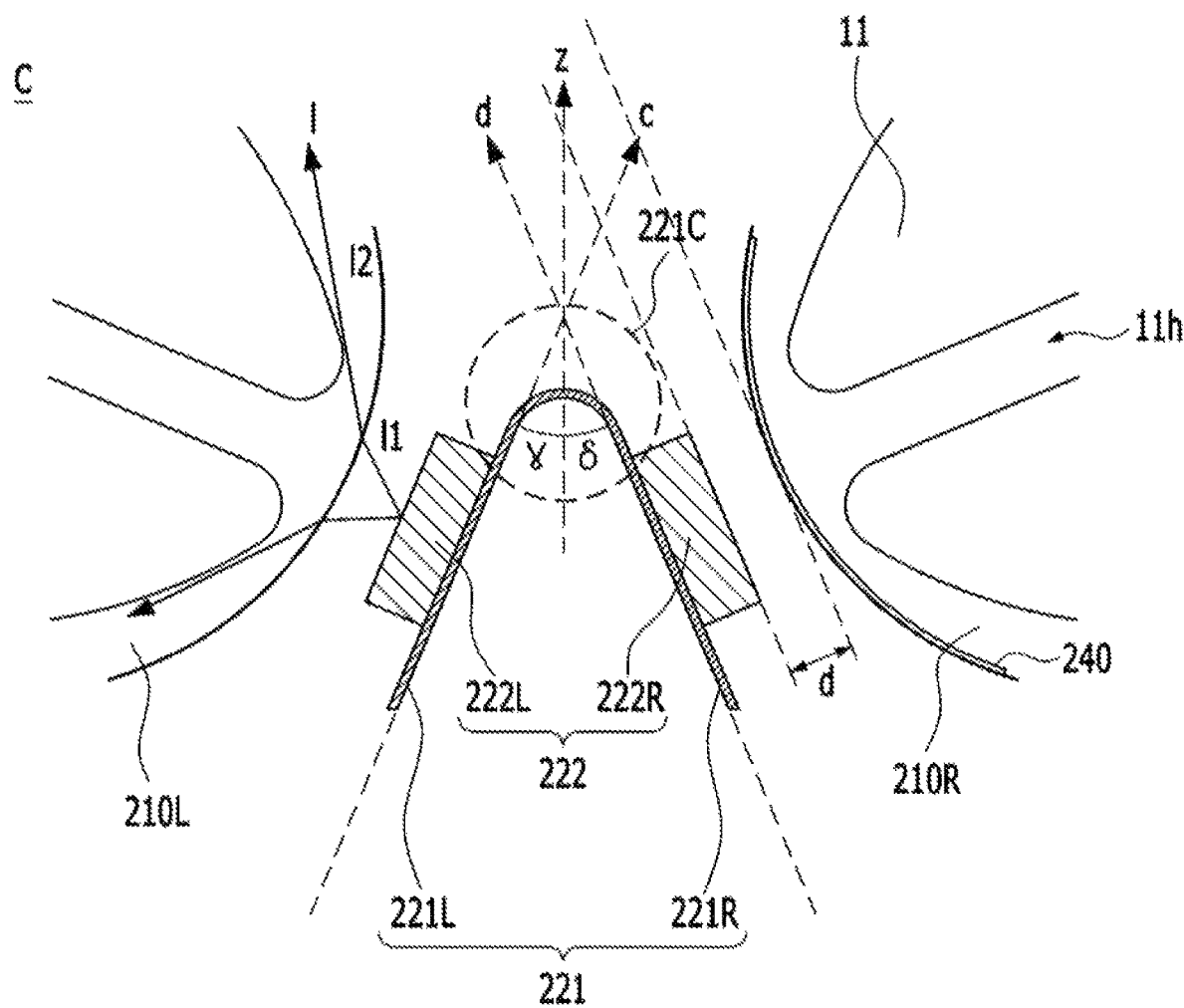
FIG. 6 is a detailed diagram illustrating the portion "C" of FIG. 3.

FIG. 6 is a detailed diagram illustrating the portion "C" of FIG. 3.

Although the lens 223 is not shown in FIG. 6 for convenience of description, it is assumed that the following embodiments include the lens 223. Also, in the same manner as in FIG. 4, "z" may denote the central axis for the height direction of the electronic device 200. In FIG. 6, "c" may denote a parallel axis of a first surface 221L, and "d" may denote a parallel axis of a second surface 221R.

As shown in FIG. 6, the wiring substrate 221 may be formed of, for example, a flexible material. The wiring substrate 221 may be bent at least once. The wiring substrate 221 may include a first surface 221L, a second surface 221R, and a bent portion 221C for connecting the first surface 221L to the second surface 221R. That is, a top surface of the first surface 221L and a top surface of the second surface 221R are connected to each other through the bent portion 221C, but the first surface 221L and the second surface 221R may be directed in different directions.

Specifically, the first surface 221L is formed to be inclined by a preset angle ($\gamma$) with respect to the central axis (z) of the height direction of the electronic device 200. Also, the second surface 221R is formed to be inclined by a preset angle ($\delta$) with respect to the central axis (z) of the height direction of the electronic device 200. In this case, each of $\gamma$ and $\delta$ may be a real number between 0° and 90°. In addition, when $\alpha$ and $\beta$ described in FIG. 4 have the same value, $\gamma$ and $\delta$ may also have the same value. When $\alpha$ and $\beta$ described in FIG. 4 are different from each other, $\gamma$ and $\delta$ may have different values.

As described above, the electronic device 200 may include one wiring substrate 221 to reduce production costs. In addition, the electronic device 200 may set an optimal slope for the head holder (e.g., 210L or 210R) using the flexible wiring substrate 221.

Meanwhile, unlike shown in FIG. 6, when the wiring substrate 221 is not formed of a flexible material, the wiring substrate 221 may include two wiring substrates. For example, the wiring substrate 221 may include a first wiring substrate corresponding to the first surface 221L and a second wiring substrate corresponding to the second substrate 221R.

The light source 222 may include a first light source 222L disposed on the first surface 221R, and a second light source 222R disposed on the second surface 221L. The first light source 222L may be formed to face the first head holder 210L, and may emit light toward the first head holder 210L. The second light source 222R may be formed to face the second head holder 210R, and may emit light toward the second head holder 210R. That is, the light source 222 may include light sources (e.g., 222L and 222R) respectively corresponding to the holders 210. Accordingly, the number of light sources 222 may correspond to the number of the holders 210.

At this time, the light L1 emitted from the light source 222 goes straight toward the holder 210. The emitted light L1 may be refracted at a predetermined angle while being transmitted through the lens 223. That is, light L2 having passed through the lens may go straight within the head holder 210 at a preset angle different from that of the emitted light L1, and may then arrive at the head 11 of the wearable device.

As described above, light emitted from the light source 222 may arrive at the holder 210 after passing through the lens 223. At this time, in order for the emitted light to more effectively reach the head 11 of the wearable device, the light source 222 may be spaced apart from the head 11 of the wearable device by a predetermined distance (d) or more. Thereby, the electronic device 200 may provide a sufficient space in which light can be refracted, so that light can sufficiently reach the outer portion (where it is difficult for light emitted from the light source 222 to reach the outer portion of the head 11 by performing light propagation once) of the head 11 of the wearable device.

The light source 222 may be spaced apart from the head 11 of the wearable device by a first distance (d), but may be spaced apart from the head 11 of the wearable device by a second distance or less (not shown). The first distance (d) may be, for example, 2 mm. The second distance may be a point where sterilization power of light emitted from the light source 222 is significantly degraded.

In this case, the electronic device 200 may further include a sensor (e.g., the sensing unit described in FIG. 2). The sensor may sense the distance from the light emitting unit 220 to the wearable device 200. For example, the sensor may sense whether the distance from the light emitting unit 220 to the wearable device 200 is between the first distance (d) and the second distance. Preferably, the sensor may sense whether the distance from the light emitting unit 220 to the wearable device 200 is a predetermined distance (d).

When the electronic device 200 determines that the wearable device 200 is disposed within the range of a proper distance (e.g., a preset distance between the first distance and the second distance, preferably the first distance) through the sensor, the wearable device 200 is sterilized by controlling the light emitting unit 220.

In contrast, when the electronic device 200 determines that the distance measured by the sensor is not a proper distance (e.g., when the wearable device 200 is located at a predetermined second distance or more from the light emitting unit), the electronic device 200 may output an alarm sound through the output unit 150 shown in FIG. 2. That is, the electronic device 200 outputs a sound signal indicating that the wearable device 200 is not properly mounted through, for example, the sound output module 152.

Through this, the electronic device 200 may allow the wearable device 10 to be disposed at a proper location within the electronic device 200, so that the electronic device 200 can be efficiently sterilized.

As described above, the electronic device 200 according to the embodiments may be configured in a manner that each light source 222 is disposed in each head holder (e.g., 210L or 210R), so that light (l) emitted from the light source 222 can reach a portion of the body 12 of the wearable device as well as all or some of the head 11 of the wearable device disposed in each head holder.

Meanwhile, the holder 210 may further include a reflection unit 240. The reflection unit 240 may be at least a portion of the inner surface of the holder 210, and may be provided in a direction facing the wearable device 10. As shown in FIG. 6, the reflection unit 240 may be provided to cover the entire inner surface of the holder 210. For example, the inner surface of the holder 210 may be formed of a glossy surface with high reflectivity. Alternatively, unlike FIG. 6, the reflection units 240 may be spaced apart from each other by a predetermined distance while having the same or different sizes, thereby covering a portion of the inner surface of the holder 210.

The reflection unit 240 may be formed of a material having a reflectivity greater than or equal to a predetermined reflectivity. For example, the reflection unit 240 may allow all or some of light emitted from the light source 222 to be reflected by the reflection unit 240. The electronic device 200 may allow the light (L2) having penetrated the lens to be reflected by the reflection unit 240 so that all or some of the head 11 of the wearable device can reach some regions of the body 12 of the wearable device. Accordingly, the electronic device 200 may increase the size of the region where the light emitted from the light source 222 can reach.

As described above, the electronic device 200 may sterilize the wearable device 10 by directly emitting light from the light source 222 toward the wearable device 10. That is, the electronic device 200 may sterilize not only the headhole 11h of the wearable device disposed at a position located opposite to the light source 222, but also the entirety of the head 11 of the wearable device and/or the body 12 of the wearable device. As a result, the electronic device 200 may sterilize all or most areas of the wearable device 10 contacting the user's ear. In addition, the electronic device 200 provides excellent sterilization power.

FIGS. 7(a) to 7(c) are diagrams illustrating guides of the electronic device according to the embodiments of the present disclosure.

FIG. 7(a) is a top view illustrating the holder 210 in which guides 211 and 212 are disposed. In addition, FIG. 7(b) is an enlarged view of the portion A1 of FIG. 7(a), and FIG. 7(c) is an enlarged view of the portion A2 of FIG. 7(a).

Figure 7:
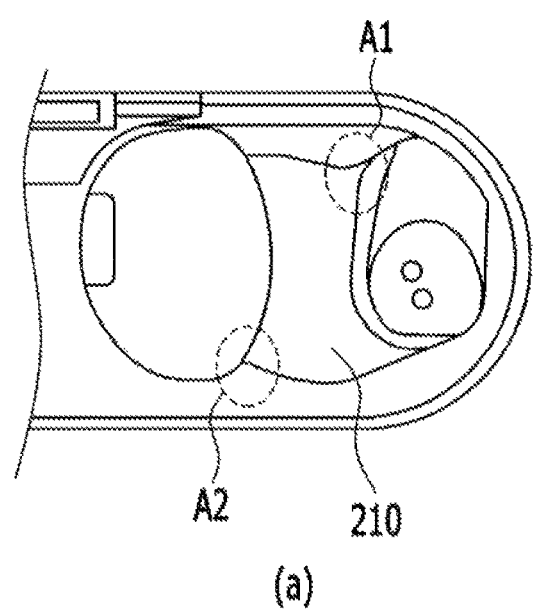
FIGS. 7(a) to 7(c) are diagrams illustrating guides of the electronic device according to the embodiments of the present disclosure.
Figure 7:
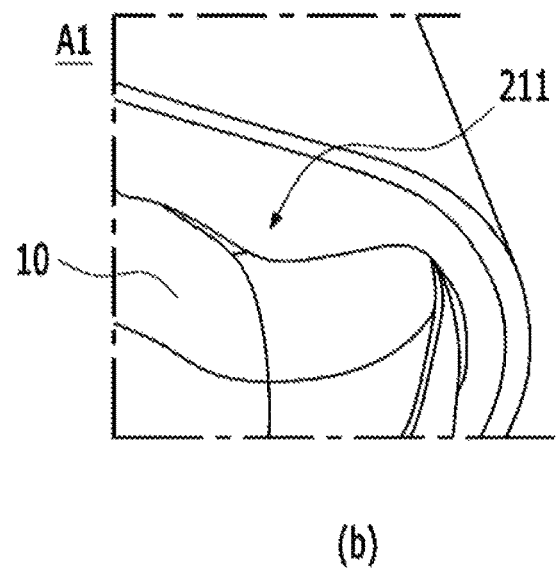
Figure 7:
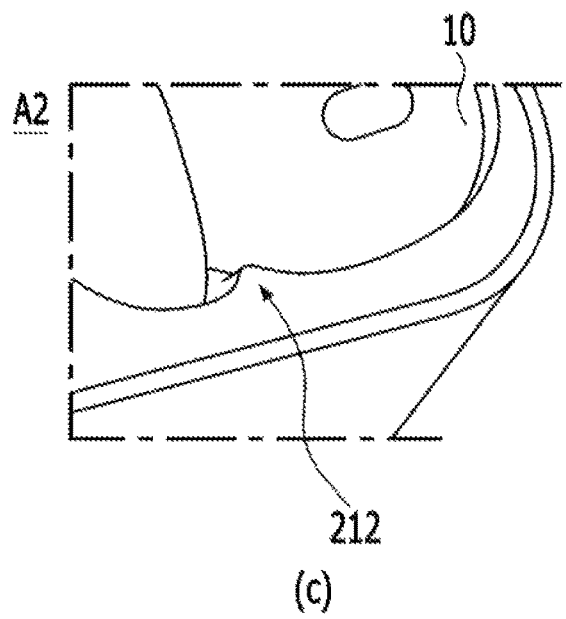

As described in FIG. 6, the wearable device 10 may be spaced apart from the light emitting unit 220 by a predetermined distance or more. Specifically, the wearable device 10 may be disposed to be spaced apart from the light source 222 by a predetermined distance or more. To this end, the electronic device 200 may include a guide (e.g., 211, 212). The guide may include one or more guides. For example, the guide may include a first guide 211 and a second guide 212. Although FIG. 7 illustrates two guides 211 and 212 for convenience of description, the position, number, and shape of the guides are not limited to those shown in FIG. 7.

The guides 211 and 212 may guide the position of the wearable device 10 mounted in the holder 210. The guides 211 and 212 may allow the wearable device 10 to be mounted and supported at a preset position. The holder 210 has a shape corresponding to at least a portion of the appearance of the wearable device 10. At this time, the guides 211 and 212 may protrude from a portion of the inner surface of the holder 210. That is, the guides 211 and 212 may allow the wearable device 10 to be hung, fixed, or supported through the protrusion portion.

For example, as shown in FIG. 7(b), the first guide 211 may be formed at a position corresponding to a portion of the body 10b of the wearable device. For example, the first guide 211 may be formed at a portion corresponding to a curvature portion of the body 10b of the wearable device such that the wearable device 10 can be fixed and/or supported in the left and right directions (i.e., a horizontal direction) thereof.

Alternatively, for example, as shown in FIG. 7(c), the second guide 212 is formed at a position corresponding to a connection portion between the head 10h and the body 10b of the wearable device. For example, the second guide 212 may be formed at a portion corresponding to the end portion of the body 10b of the wearable device, so that the wearable device 10 can be fixed and/or supported in the left and right directions.

Meanwhile, each of the guides 211 and 212 may be formed in a hook shape. In this case, each of the guides 211 and 212 can allow the wearable device 10 to be more effectively worn on the ear and fixed to the earhole. Alternatively, the guides 211 and 212 may have the properties of absorbing the wearable device 10. For example, the guides 211 and 212 may have magnetism that can interact with the wearable device 10. In this case, the guides 211 and 212 may be adsorbed to the wearable device 10, thereby improving the effects of fixing and/or supporting the wearable device 10.

As described above, the electronic device 200 may guide the position of the wearable device 10 with respect to the electronic device 200 using the shape of the seating portion of the wearable device 10. Accordingly, the electronic device 200 can more efficiently implement the effects described in FIG. 6.

Figure 8:
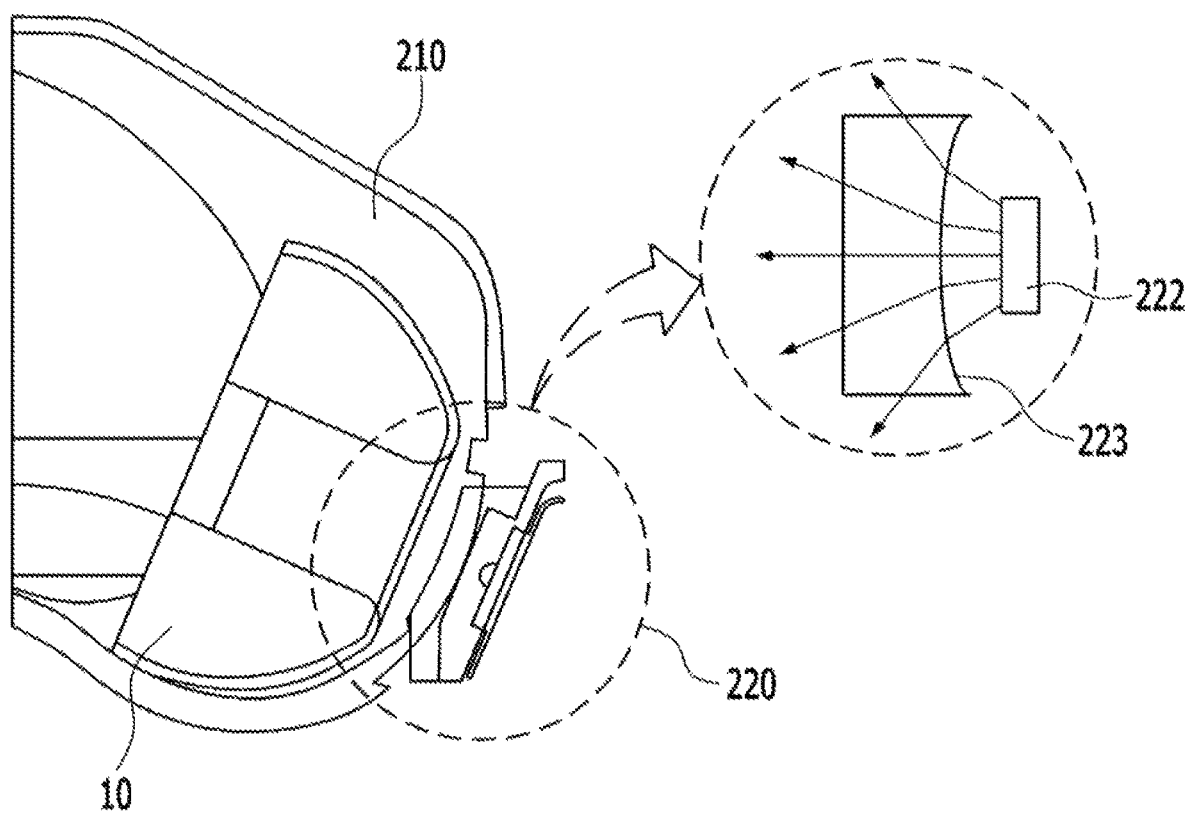
FIG. 8 is a diagram illustrating a lens of the electronic device according to the embodiments of the present disclosure.

FIG. 8 is a diagram illustrating the lens of the electronic device according to the embodiments of the present disclosure.

FIG. 8 is a view illustrating the holder 210 in which the wearable device 10 is mounted, a light emitting unit 220 that emits light toward the holder 210, and an enlarged view of the light emitting unit 220.

At least a portion of the lens 223 may include a concave surface. That is, a portion of the lens 223 may be formed to have a concave surface where light emitted from the light source 222 is incident and light passes therethrough. As a result, the lens 223 may diffuse incident light.

The lens 223 may include a material having a higher refractive index than air. Accordingly, the concave lens 223 may penetrate the lens 223 by changing a refraction angle of at least a portion of light being incident toward the lens 223 after passing through the air. A detailed description thereof is the same or similar to those described in FIG. 6 or FIG. 10.

That is, the concave lens 223 may diffuse light emitted from the light source 222 such that the range of light emitted from the light source 222 to the inside of the holder 210 can be enlarged. In particular, this structure can be considered more effective as transmittance of the head 11 of the wearable device is gradually reduced.

Alternatively, differently from those shown in FIG. 8, the lens 223 may be formed convexly toward the light source 222. In this case, the lens 223 can increase the amount of transmitted light by collecting light emitted from the light source 222. Alternatively, unlike FIGS. 4 to 8, the lens 223 may be omitted. In this case, the embodiments can minimize the amount of light lost by the lens 223. Specifically, the above-described structure may be considered more effective as transmittance of the head 11 of the wearable device gradually increases. A portion of the lens 223 may have a partially concave shape or a partially convex shape.

Through the above-described structure, the electronic device 200 according to the embodiments can allow light to evenly reach the head 11 of the wearable device, thereby improving sterilization power of the wearable device 10.

The light source 222 and the wiring substrate 221 are exposed to the exterior portion provided with the holder 210 through the lens 223. That is, the constituent elements of the light emitting unit 220 including the light source 222 and the wiring substrate 221 are not directly exposed to the outside. Accordingly, the electronic device 200 according to the embodiments provides a structure with improved appearance quality.

Figure 9:
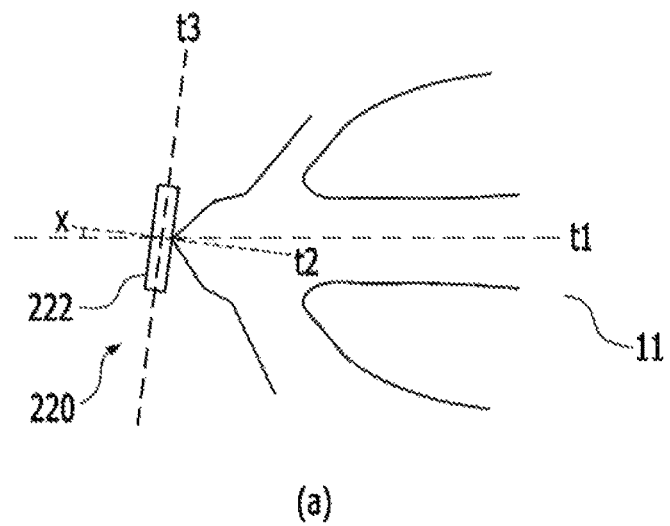
FIG. 9 is a diagram illustrating the degree of inclination of a light emitting unit according to the embodiments of the present disclosure.
Figure 9:
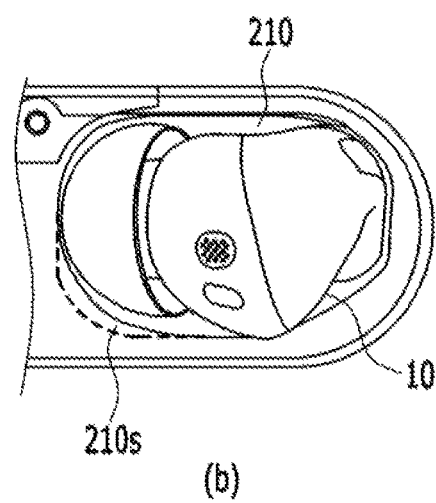

FIG. 9 is a diagram illustrating the degree of inclination of a light emitting unit according to the embodiments of the present disclosure.

FIG. 9(a) is a view illustrating that the light emitting unit is tilted with respect to the head 11 of the wearable device.

FIG. 9(a) is a view illustrating only the light source 222 included in the light emitting unit and the head 11 of the wearable device for convenience of description. In FIG. 9(a), 't1' denotes the central axis of the head 11 of the wearable device, and corresponds to 'a' or 'b' shown in FIG. 4. In addition, 't1' denotes the central axis of the head holder 210h. In addition, in FIG. 9(a), 't2' denotes the central axis of the light emitting unit 220. For example, when the light emitting unit 220 includes only one light source, 't2' denotes the central axis of the light source 222. For convenience of description, FIG. 9 illustrates an exemplary case in which the light emitting unit 220 includes only one light source. In FIG. 9(a), 't3' denotes an axis parallel to the light emitting unit. For example, 't3' may correspond to 'c' or 'd' shown in FIG. 6.

The wearable device 10 may not be formed in a shape in which all surfaces of the wearable device 10 are formed line-symmetrically to the central axis (t1) of the head. In addition, in order for the wearable device 10 to be stably disposed in the holder 210, the holder 210 may be formed as a groove having different shapes in the front and rear directions, as shown in FIG. 3. In this case, when the central axis (t2) of the light emitting unit coincides with the central axis (t1) of the head of the wearable device, light emitted from the light source 222 may unevenly reach the head 11 of the wearable device. Accordingly, in this case, a method for allowing light emitted from the light source 222 to evenly reach the head 11 of the wearable device is required.

As shown in FIG. 9(a), the light emitting unit 220 may be formed to be tilted by a preset angle (x) or less with respect to the central axis (t1) of the holder 210. In other words, the central axis (t2) of the light emitting unit may be tilted by a slope between 0° and the preset angle (x) with respect to the central axis (t1) of the head of the wearable device. That is, the light sources 222 may be arranged to face the headhole 11h of the wearable device, and may not be arranged completely opposite to each other.

FIG. 9(b) is a top view illustrating the holder 210 in which the wearable device 10 is mounted.

As the light emitting unit 220 is inclined with respect to the head holder 210b, light emitted from the light emitting unit 220 may not reach at least a portion of the head 11 of the wearable device. Therefore, when the light emitting unit 220 is provided with a slope less than the preset angle (x), the holder 210 may change the internal shape thereof as shown in FIG. 9(b).

That is, the electronic device 200 may further form grooves 210s each having a predetermined size and a predetermined shape inside the holder 210. At this time, each of the grooves 210s may have a size in which the wearable device 10 and the inside of the holder 210 can be guaranteed. For example, each of the grooves 210s may be a space in which a minimum distance between the head 11 of the wearable device (disposed in a side where the grooves 210s are formed) and the light source 222 is a proper distance described in FIG. 6.

As described above, the electronic device 200 can uniformly sterilize the wearable device 10 having a three-dimensional (3D) shape through the inclined light emitting unit 220 and the front and rear asymmetric holder 210.

FIG. 9 is a conceptual diagram illustrating a method for positioning the wearable device 10 in a region where light emitted from the light emitting unit 220 has reached. A method for allowing light emitted from the light emitting unit 220 to penetrate the lens 223 without being reflected by the lens 223 will hereinafter be described in detail.

Figure 10:
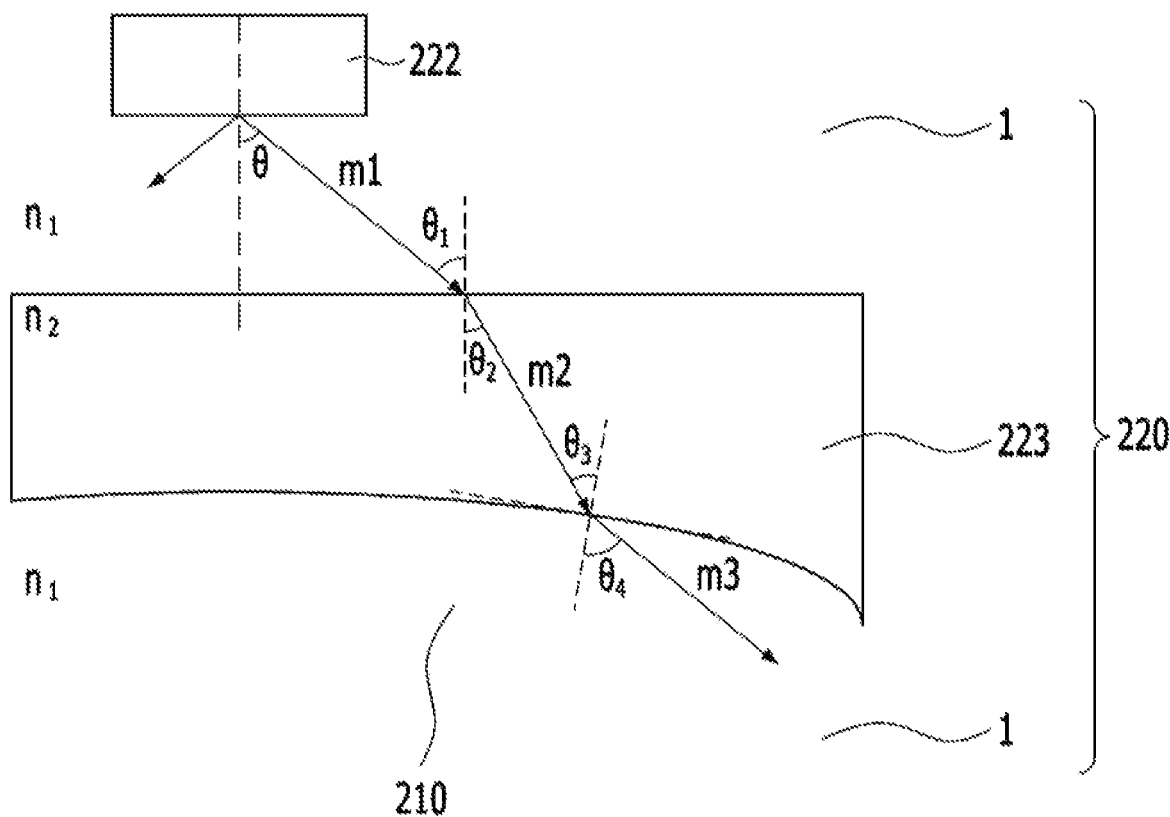
FIG. 10 is a diagram illustrating an irradiation angle of the light emitting unit according to the embodiments of the present disclosure.

FIG. 10 is a diagram illustrating an irradiation angle of the light emitting unit according to the embodiments of the present disclosure.

For convenience of explanation, only the light source 222 and the lens 223 among the constituent components of the light emitting unit 220 are shown in FIG. 10. In FIG. 10, reference numeral '1' may denote the air, and reference numeral 223 may denote the lens. In FIG. 10, 'm1' may denote light emitted from the light source 222, 'm2' may denote light passing through the lens, and 'm3' may denote light having penetrated the lens.

As shown in FIG. 10, the light source 222 may emit light (m1) with a preset irradiation angle ($\theta$). In this case, the irradiation angle may be an angle between the emitted light (m1) and the direction perpendicular to the surface of the lens 223. If total reflection of the emitted light (m1) does not occur, the light (m1) goes straight toward the holder 210 after passing through the lens 223 as shown in FIG. 10.

Specifically, the light (m1) emitted from the light source 222 may be incident upon the surface of the lens 223 with an angle ($\theta_1$) of incidence. At this time, if the surface of the light source 222 is parallel to the surface of the lens 223, $\theta$ is equal to $\theta_1$. In this case, $\theta_1$ is an angle where light can be refracted into the lens without being totally reflected from the surface of the lens 223. When the light is refracted into the lens 223, light (m2) passing through the lens may proceed toward the holder 210 with an angle ($\theta_2$) of refraction. The light (m2) passing through the lens is incident upon the surface of the lens 223 with an angle ($\theta_3$) of incidence. In this case, $\theta_3$ is an angle where light can be refracted toward the outside of the lens 223 without being totally reflected by the surface of the lens 223. The light (m3) transmitted from the lens may proceed toward the holder 210 with an angle ($\theta_4$) of refraction.

In this case, as the angle ($\theta_4$) increases, the range of light diffused into the holder 210 also increases. Thus, in order to maximize the angle ($\theta_4$), there is a need for light to be incident upon the surface of the lens 223 with a maximum angle ($\theta_3$). On the other hand, when the angle ($\theta_3$) is set to a critical angle or more, light (m2) having penetrated the lens 223 may be totally reflected from the surface of the lens 223 without proceeding from the lens 223 to the air 1. In this case, the critical angle refers to an incident angle where total reflection occurs when light is incident in the direction from a material having a high refractive index to another material having a low refractive index. Therefore, there is a need for the angle ($\theta_3$) to have the size corresponding to the critical angle or less, so that light should be incident upon the surface of the lens with a maximum angle ($\theta_3$).

In this case, the critical angle ($\theta_3$) can be calculated by Equation 1 below.

$$\sin\theta_3 = \frac{n_{air}}{n_{lens}} \qquad \text{[Equation 1]}$$

In this case, $n_{air}$ may denote the refractive index of the air 1, and $n_{lens}$ may denote the refractive index of the lens 223. For example, if $n_{lens}$ is set to 1.16, the critical angle ($\theta_3$) is set to 42.15°. Thus, considering that the angle ($\theta_3$) is set to 42.15° or less, the light source 222 enables the light (m1) to be irradiated with a maximum irradiation angle within the corresponding range. However, when the medium between the light source 222 and the lens 223 is changed to another medium other than the air, $n_{air}$ in Equation 1 can be substituted with the refractive index of any other medium.

Through the above-described structure and design, the electronic device 200 according to the embodiments may emit light toward the holder 210 and all or almost all areas of the head 11 of the wearable device mounted in the holder 210. Accordingly, the embodiments provide an efficient sterilization function.

The electronic device 200 may apply all of the configurations described in FIGS. 9 and 10, or may apply only one configuration. Hereinafter, a method of manufacturing the light emitting unit 220 will be described in detail.

Figure 11:
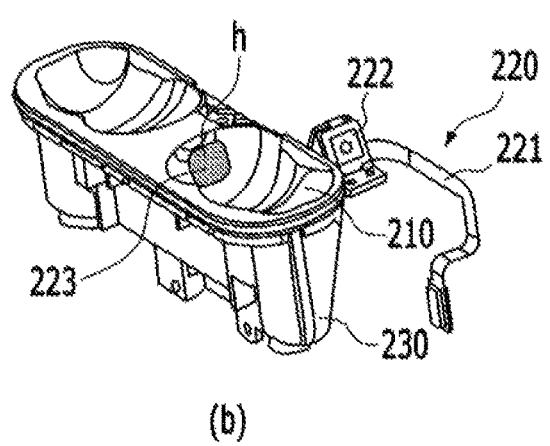
FIG. 11 is a diagram illustrating an example of a structure of the light emitting unit according to the embodiments of the present disclosure.
Figure 11:
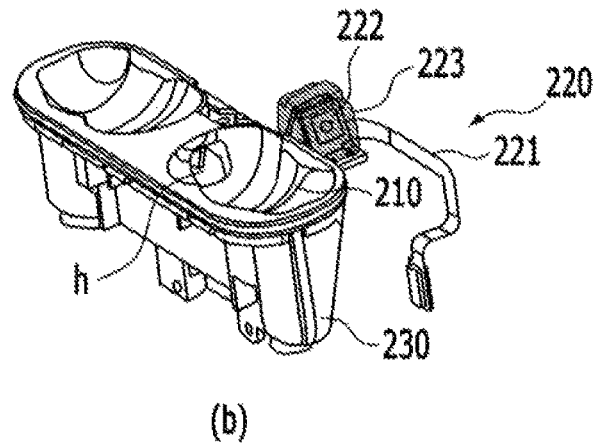

FIG. 11 is a diagram illustrating an example of a structure of the light emitting unit according to the embodiments.

FIG. 11 illustrates a method for disposing the light emitting unit 220 in the housing 230. As can be seen from FIGS. 3 to 10, the holder 210 may include a hole (h) through which light emitted from the light emitting unit 220 can pass. The hole (h) may be provided to correspond to the light emitting unit 220.

FIG. 11(a) is a diagram illustrating the lens 223 is first provided in the housing 230 and the light emitting unit 220 is assembled with the housing 230.

The lens 223 may be assembled to cover the hole (h) formed in the housing 230. For example, the lens 223 may be formed by a double injection method in which the housing 230 including the hole (h) is first manufactured and the lens 223 is formed to cover the hole (h). Through this manufacturing method, each of the housing 230 and the lens 223 is formed with high precision and high durability.

The light emitting unit 2230 may be assembled at a position corresponding to the hole (h) with respect to the housing 230 in which the lens 223 is formed. As described above, the lens 223 and the light emitting unit 220 are assembled separately from each other. Thus, although the problem occurs in the light source 222 of the electronic device 200, the light source 222 can be easily replaced with another.

FIG. 11(b) is a diagram illustrating an example in which the light emitting unit 220 including the lens 223 is assembled to the housing 230.

Unlike the embodiment illustrated in FIG. 11(a), the lens 223 is provided on the wiring substrate 221 to cover the light source 222, and is then assembled to the housing 230. The lens 223 may be injection-fixed to the wiring substrate 221. In this case, a space between the lens 223 and the light source 222 is sealed, so that foreign materials can be prevented from entering the space from the outside.

Accordingly, the electronic device 200 according to the embodiments may allow the light emitting unit 220 including the light source 222 to realize a waterproof function. Furthermore, when the waterproof function is performed on the light emitting unit 220 provided with the lens 223, the embodiments can provide a more improved waterproof function. In this case, the embodiments can provide the improved electronic device 200 with higher durability.

Hereinafter, another embodiment in which the light emitting unit 220 is disposed between the first holder 210L and the second holder 210R, but has a different structure from the above-described embodiment will be described with reference to the attached drawings.

Figure 12:
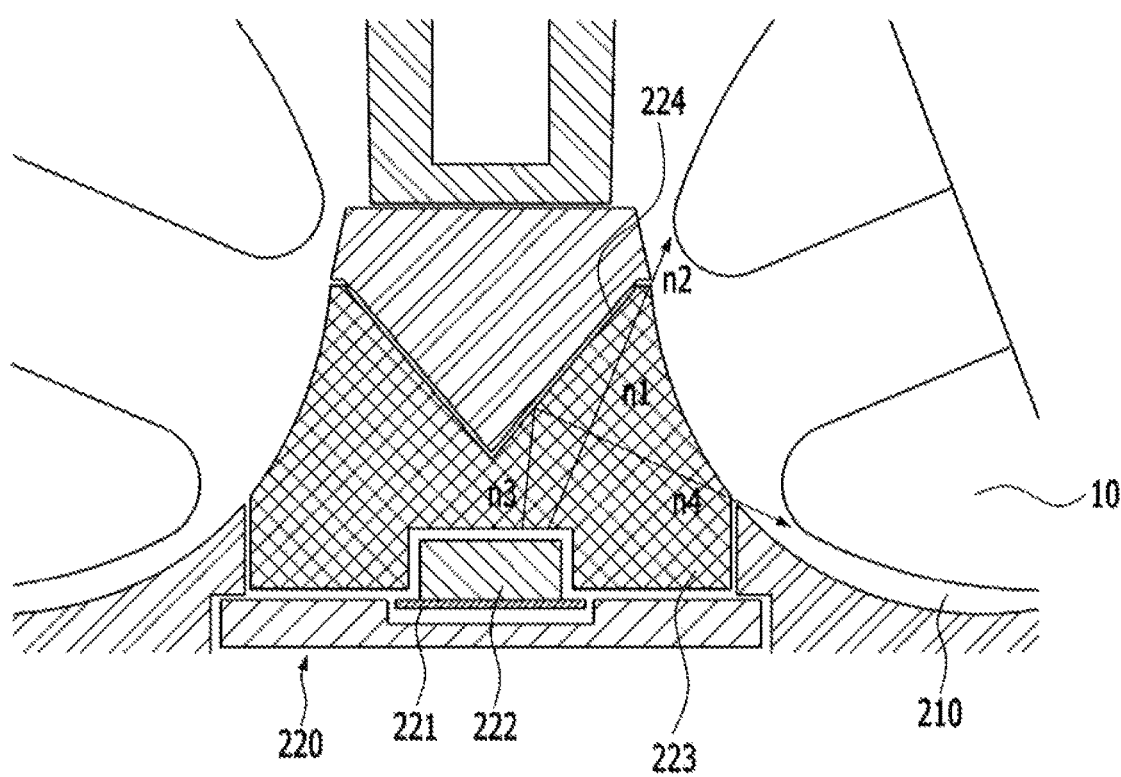
FIG. 12 is a cross-sectional view illustrating another example of the wearable device taken along the line A-A' shown in FIG. 3.

FIG. 12 is a cross-sectional view illustrating another example of the wearable device taken along the line A-A' shown in FIG. 3.

FIG. 12 illustrates the electronic device 200 having a structure different from that of FIGS. 5 and 6. However, the embodiment of FIG. 12 is different from the above-described embodiments in terms of only the internal arrangement of the light emitting unit, and the remaining elements other than the light emitting unit of FIG. 12 are identical or similar to those of the above-described embodiments.

Referring to FIG. 12, the light emitting unit 220 may be disposed between the first holder 210L and the second holder 210R. The light emitting unit may include a wiring substrate 221, a light source 222, a lens 223, and a mirror 224.

The wiring substrate 221 may be formed on a vertical plane in the height direction of the electronic device 200. The wiring substrate 221 may include a flat-type wiring substrate or a flexible-type wiring substrate. The wiring substrate 221 may be electrically connected to the light source 222, and may transmit the electrical signal to the light source 222.

The light source 222 may be provided on the wiring substrate 221. Accordingly, the light source 222 is also disposed on a vertical plane in the height direction of the electronic device 200. That is, the light source 222 is disposed to face the top surface of the electronic device 200 and emits the lights (n1, n3) toward the top surface of the electronic device 200.

The mirror 224 may include a material having a high reflectivity. The mirror 224 may be formed on the top surface of the lens 223 to face the light source 222. The mirror 224 may protrude from the top surface of the lens 223 in the direction of the light source 222. That is, the mirror 224 is provided in a position, an angle, and a shape that can reflect light emitted from the light source 222 toward the holder 210. For example, as shown in FIG. 12, the mirror 224 may be formed in a conical shape in which a vertex is disposed to face the bottom surface of the wearable device.

For example, the light (n1) emitted from the light source 222 may penetrate the lens 223, or may be refracted by the lens 223 and then proceed toward the holder 210 as denoted by the light (n2). Alternatively, for example, the light (n3) emitted from the light source 222 may penetrate the lens 223, may be reflected by the mirror 224, and may proceed toward the holder 210.

That is, the light emitting unit 220 refracts light through the lens 223 or reflects light through the mirror 224 to diffuse the light toward the holder 210. Through this, the electronic device 200 can sterilize all or some of the head of the wearable device 10 and/or a portion of the body of the wearable device 10.

In addition, the electronic device 200 according to the embodiments of the present disclosure may sterilize the plurality of holders 210 through only one light source 222. Accordingly, the electronic device 200 improves material costs and assemblability.

The electronic device according to the embodiments may sterilize all or some of the head (e.g., the eartip) of the wearable device, and/or some parts of the body of the wearable device. In addition, the electronic device proposes an optimal arrangement method of internal components of the electronic device to sterilize the wearable device.

The detailed description of the electronic device according to the embodiments of the present disclosure has been given to enable those skilled in the art to implement and practice the invention. Although the electronic device according to the embodiments has been described with reference to the preferred examples, those skilled in the art will appreciate that various modifications and variations can be made in the present disclosure without departing from the spirit or scope of the present disclosure described in the appended claims. Accordingly, the present disclosure should not be limited to the specific examples described herein, but should be accorded the broadest scope consistent with the principles and novel features disclosed herein.

A person skilled in the art may practice unspecified embodiments by combining or substituting the disclosed embodiments, without departing from the scope of the present disclosure. It will be apparent to those skilled in the art that various modifications and variations can be made in the present disclosure without departing from the spirit or scope of the invention. Thus, it is intended that the present disclosure cover the modifications and variations of this invention provided they come within the scope of the appended claims and their equivalents.

As is apparent from the above description, the electronic device according to the embodiments of the present disclosure can sterilize the wearable device.

The electronic device according to the embodiments of the present disclosure can sterilize the inside or outside of the eartip of the wearable device.

The electronic device according to the embodiments of the present disclosure can prevent inflammation from occurring in the user's ear due to wearing of the wearable device.

The electronic device according to the embodiments of the present disclosure can improve the quality of appearance thereof.

The electronic device according to the embodiments of the present disclosure can implement a waterproof function.

It will be apparent to those skilled in the art that various modifications and variations can be made in the present disclosure without departing from the spirit or scope of the inventions. Thus, it is intended that the present disclosure covers the modifications and variations of this invention provided they come within the scope of the appended claims and their equivalents.

What is claimed is:

1. An electronic device comprising:
   a first holder comprising a first head holder and a first body holder, wherein the first head holder is structured to receive a head of a first wearable device and the first body holder is structured to receive a body of the first wearable device;
   a second holder comprising a second head holder and a second body holder, wherein the second head holder is structured to receive a head of a second wearable device and the second body holder is structured to receive a body of the second wearable device;
   a light emitting unit comprising a first light source and a second light source, wherein the first light source is configured to emit first UV light toward the first head holder and the second light source is configured to emit second UV light toward the second head holder; and
   a housing structured to include the first holder, the second holder and the light emitting unit,
   wherein the first head holder and the second head holder are structured to receive the head of the first wearable device and the head of the second wearable device such that a headhole of the first wearable device faces a headhole of the second wearable device, and
   wherein the light emitting unit is located between the first holder and the second holder, such that the first light source of the light emitting unit faces the headhole of the first wearable device and the second light source of the light emitting unit faces the headhole of the second wearable device when the first head holder and the second head holder receive the head of the first wearable device and the head of the second wearable device.

2. The electronic device according to claim 1, wherein the light emitting unit includes:
   a wiring substrate; and
   a lens structured to overlap the first light source and the second light source and being coupled to the wiring substrate,
   wherein the first light source and the second light source are formed on the wiring substrate and being electrically coupled to the wiring substrate to emit the first UV light and the second UV light.

3. The electronic device according to claim 2, wherein:
   the wiring substrate includes a first surface, a second surface, and a bent portion for connecting the first surface to the second surface,
   wherein the first light source is disposed on the first surface to emit the first UV light toward the first head holder, and the second light source is disposed on the second surface to emit the second UV light toward the second head holder.

4. The electronic device according to claim 3, wherein:
   a central axis of the first light source is not parallel with a central axis of the first head holder.

5. The electronic device according to claim 2, wherein:
   at least a portion of the lens is structured as a concave surface.

6. The electronic device according to claim 2, wherein:
   the lens is coupled to the wiring substrate,
   the lens includes waterproofing, and
   the lens is connected to the first holder and the second holder.

7. The electronic device according to claim 1, wherein the first holder further includes:
   a first guide formed to contact the head of the first wearable device, wherein the first guide creates distance between the light emitting unit and the first-head of the first wearable device; and
   wherein the second holder further includes:
   a second guide formed to contact the head of the second wearable device, wherein the second guide creates distance between the light emitting unit and the head of the second wearable device.

8. The electronic device according to claim 1, wherein at least a portion of an inside of the first head holder and at least a portion of an inside of the second head holder include:
   a reflection element respectively formed to reflect the first UV light emitted by the light emitting unit toward the first head holder and reflect the second UV light emitted by the light emitting unit toward the second head holder.

9. The electronic device according to claim 1, further comprising:

a sensor configured to sense whether any of the first wearable device and the second wearable device is located within a defined distance from the light emitting unit.

* * * * *